(12) United States Patent
Landry

(10) Patent No.: US 8,488,952 B2
(45) Date of Patent: Jul. 16, 2013

(54) AROMATIC VAPORIZER

(75) Inventor: Forrest Landry, Rancho Santa Fe, CA (US)

(73) Assignee: Magic-Flight General Manufacturing, Inc., San Diego, CA (US)

( * ) Notice: Subject to any disclaimer, the term of this patent is extended or adjusted under 35 U.S.C. 154(b) by 509 days.

(21) Appl. No.: 12/705,906

(22) Filed: Feb. 15, 2010

(65) Prior Publication Data

US 2010/0322599 A1    Dec. 23, 2010

Related U.S. Application Data

(60) Provisional application No. 61/219,051, filed on Jun. 22, 2009.

(51) Int. Cl.
*A01G 13/06*    (2006.01)

(52) U.S. Cl.
USPC ........................ 392/386; 128/203.27

(58) Field of Classification Search
USPC ..................................... 128/203.27
See application file for complete search history.

(56) References Cited

U.S. PATENT DOCUMENTS

| | | | |
|---|---|---|---|
| 437,070 A | 9/1890 | Wiesebrock | |
| 2,104,266 A | 1/1938 | McCormick | |
| 3,117,210 A | 1/1964 | Herb | |
| 3,949,743 A * | 4/1976 | Shanbrom | 128/200.14 |
| 4,036,224 A | 7/1977 | Choporis et al. | |
| 4,141,369 A * | 2/1979 | Burruss | 131/330 |
| 4,303,083 A | 12/1981 | Burruss, Jr. | |
| 5,665,262 A | 9/1997 | Hajaligol et al. | |
| 5,730,158 A * | 3/1998 | Collins et al. | 131/194 |
| 5,819,756 A | 10/1998 | Mielordt | |
| 6,181,874 B1 * | 1/2001 | Ireland et al. | 392/497 |
| 6,481,437 B1 | 11/2002 | Pate | |
| 6,761,164 B2 | 7/2004 | Amirpour et al. | |
| 6,772,756 B2 * | 8/2004 | Shayan | 128/203.26 |
| 7,088,914 B2 | 8/2006 | Whittle et al. | |
| 7,228,067 B2 * | 6/2007 | Magni et al. | 392/480 |
| 7,434,584 B2 | 10/2008 | Steinberg | |
| 7,445,007 B2 | 11/2008 | Balch et al. | |
| 7,475,684 B2 | 1/2009 | Balch et al. | |
| 7,624,734 B2 | 12/2009 | Balch et al. | |
| 7,766,013 B2 * | 8/2010 | Wensley et al. | 128/203.27 |
| 8,042,550 B2 | 10/2011 | Urtsev et al. | |
| 2003/0217750 A1 * | 11/2003 | Amirpour et al. | 128/203.25 |
| 2005/0117895 A1 * | 6/2005 | Balch et al. | 392/386 |
| 2006/0283449 A1 | 12/2006 | Balch et al. | |
| 2009/0032034 A1 | 2/2009 | Steinberg | |
| 2009/0041442 A1 * | 2/2009 | Rouse, Jr. | 392/386 |
| 2009/0078253 A1 * | 3/2009 | Bao | 128/203.26 |
| 2009/0293888 A1 | 12/2009 | Williams et al. | |
| 2010/0074603 A1 * | 3/2010 | Balch et al. | 392/387 |
| 2010/0166397 A1 * | 7/2010 | De Luca | 392/416 |
| 2011/0079179 A1 * | 4/2011 | Okura | 118/726 |
| 2012/0255546 A1 * | 10/2012 | Goetz et al. | 128/202.21 |

OTHER PUBLICATIONS

California NORML, Press Release, Jan. 8, 2001, 2-pages, http://www.bestvaporizers.com/herbal-vaporizer.html, published to the Internet.

* cited by examiner

*Primary Examiner* — Thor Campbell
(74) *Attorney, Agent, or Firm* — Richard A. Clegg

(57) ABSTRACT

The embodiments described are directed to a vaporizer having a housing with a vaporizing chamber formed therein. A fine mesh conductive screen is disposed inside the vaporizing chamber for generation of heat through electrical resistance. The housing includes an aperture to the vaporizing chamber and an exhaust aperture for evacuating vapors by a user.

15 Claims, 4 Drawing Sheets

AROMATIC VAPORIZER

CROSS-REFERENCE TO RELATED APPLICATIONS

This application claims the benefit of U.S. Provisional Application Ser. No. 61/219,051 filed Jun. 22, 2009, which is hereby incorporated by reference in its entirety.

TECHNICAL FIELD

The embodiments described herein are generally directed to a device for vaporizing herbs and smokable materials. More particularly, it relates to a device that provides for the vaporization rather than burning of herbs and other smokeable materials which helps alleviate irritating, toxic, and carcinogenic by-products, which generally occur when such products are burned.

BACKGROUND

Smoking of naturally occurring herbs, tobacco, and other substances is a common occurrence in most countries of the world. However, the actual burning of such materials in a pipe or other smoking accessory is well known to produce carcinogenic by-products as wells as hot gasses.

Vaporization is an excellent alternative to smoking and helps reduce the harmful aspects thereof. Instead of burning the herbs, tobacco, or other products by placing them in the bowl of a pipe, which produces irritating, toxic, and carcinogenic by-products, a vaporizer heats the smoking material in a partial vacuum. This causes the active compounds contained in the plant material being employed to evaporate into a vapor.

Since during the vaporization process, no combustion occurs, substantially no smoke or taste of smoke is evident to or around the user. The exhausted vapor from the vaporizer generally contains substantially no particulate matter or tar. Further, the exhausted vapors, which are of course inhaled by the user, contain significantly lower concentrations of noxious gases such as carbon monoxide.

In use, the vapor is drawn from the vaporizer by negative air pressure created by an inhaling user. The vapor is then inhaled directly through the hose or pipe and communicated to the lungs of the user. In some cases, where the vapor is to be employed at a later time, it may be stored for subsequent inhalations in an air tight container such as a bag or jar.

Another advantage of the employment of a vaporizer, is that little to no smoke is produced. In venues which prohibit smoking primarily due to second hand smoke issues, the vaporizer thus eliminates the problem. Further, the exhausted vapors from a vaporizer are produced at cooler temperatures than smoke from combustion of the same smoked materials.

A particularly useful aspect of employing a vaporizer is that less material is required for the inhaling user to achieve a given level of effect. Thus in cases where herbs are being employed for medicinal use such as treating asthma, or for recreational use such as with tobacco, costs are greatly reduced for the user to buy the raw material for use.

As such, because there is no combustion from burning of the materials, many irritating and harmful effects of smoking are greatly reduced or eliminated. Further, since there is no actual combustion and hence no emitted smoke from a burning bowl, vaporizers are very useful in venues where there are public bans on smoking.

For instance medical marijuana use has been approved in many states of the United States and in foreign countries. A number of modern scientific studies have shown that vaporization as a delivery may be far less injurious to health than smoking over the long term. It has been shown with many medicinal herbs and cannabis, employing a high quality vaporizer will eliminate the majority of undesired compounds in the exhausted vapor.

As such, there is an ever present need for a high quality vaporizer, which may be employed in a portable fashion, for users that wish to reduce the costs of the material they must purchase as well as reduce the potential harm to themselves from the inhaled vapors by eliminating most of the harmful substances that occur during a burning of the material producing the inhaled vapors.

Conventional vaporizers commonly employ an indirect heat source upon the material being vaporized such as a flame or heating element separated by glass or a flat solid metal plate from direct contact. Many such devices employ flammable fuel and are not desirable and the indirect contact with the material being vaporized causes the need to heat a vessel to sufficient temperature to boil the essence from the herbs or other material.

Reasons that the use of a flammable fuel is not desirable include: 1) the combustion byproducts of the fuel are themselves considered harmful and as such, users should not consume these harmful byproducts; and 2) the unburned fuel itself can be a fire or safety hazard, particularly in devices that specifically employ fire or heat. As such, any device employing a burnable fuel must at a minimum support three chambers, each with unique needs and design features: 1) a chamber to store the fuel prior to burning that usually must be pressure and leak resistant; 2) a chamber or space where the fuel is consumed to produce heat that must be fireproof and heat resistant; and 3) a chamber or channel in which the vaporization itself can occur that must be user accessible and cleanable.

Moreover, a direct contact of the heat source with the material being subjected to that heat, if it prevents flame or burning would use less energy and more quickly bring the material to the correct temperature to elicit the vapors. As such, a vaporizer with direct contact of the heat source with the material being vaporized, which does not produce flame or burned material is highly desirable.

It would be further desirable to provide a vaporizer that is capable of instantly heating up in a minimal amount time. In addition, a compact design would allow the user to easily travel with the device without the typical storage concerns. As such, the portable compact unit would need to be robust and not fragile.

SUMMARY

In the embodiments and methods described, a vaporizer is employed that alleviates the shortcomings of conventional vaporizers by communicating a controlled heat source, directly with the material being vaporized, without causing a burning of the material that releases carcinogens. Employing a fine mesh conductive screen to support the material being vaporized, the device, by communicating electrical energy to the screen, heats the screen that directly heats the supported material, without causing a burning thereof. Thus, the active ingredients of the herb or other material so supported may be vaporized from the material itself prior to any combustion of the source material.

The device employs a fine metallic screen that is engaged with an electrical power source such as a battery, to form an electric heating element. This fine screen mesh, while being heated by electrical current, serves to support the herb or other material thereon overhead, concurrent with heating it. Direct contact with the material, as well as the fact that heat rises into the supported material, insures an excellent vaporization.

In an additional refinement providing utility, the electrical energy communicated to the fine screen mesh is provided at a combination of a high current level and a low voltage. This combination insures a safe electrical operation even should the fine screen mesh come into direct contact with the skin of a user. A higher voltage system would burn the user if touched and create excessive heat around the device.

Currently, the fine screen mesh is woven or knitted of conducting materials including one or a combination of materials such as copper, nickel, iron, or any wire alloys composed of these elements, such as steel and stainless steel or the like. Electrical energy in a low voltage and at a high current relative to the size of the screen is conveniently provided by batteries and a removable engagement system for the batteries with a housing supporting the fine mesh. Such batteries may be conventional in size and commercially available to make them easily replaceable.

Employing the energized fine screen mesh conductive screen in direct contact and supporting the material being vaporized allows that the screen only need be heated to a temperature sufficient to cause vaporization of the active ingredients in supported smoking materials and herbs. Combustion and related harmful particulate and carcinogens are thus avoided.

The benefits of providing a screen mesh rather than a thin formed metal plate as the heating element includes: 1) the user perceived 'taste' of the vapors is enhanced; and 2) the overall efficiency of vapor delivery to the user is increased by minimizing vapor loss from decomposition due to overheating the vapor. All vaporization systems using a heated vessel, chamber, or plate suffer from the details of what occurs when an expanding 3D volume of vapor encounters a fixed 2D or planar surface barrier formed by that vessel or plate. In a 2D or planar surface system, the position of any segment of the volume of vapor that is nearest to the 2D or planar surface system must be very nearly static, as required by gas flow boundary conditions and the physical constraint of the 2D or planar surface system itself. This in turn means any vapor so constrained is going to receive significantly more heat energy than vapor regions that are more than a short distance away and that enjoy greater degrees of freedom in motion.

This particularly occurs when the material to be vaporized is anywhere in direct contact with that 2D or planar vessel or plate. This asymmetry in the degrees of freedom of vapor in the very near vicinity of the 2D or planar surface system as compared to that of vapor farther away requires that either: 1) the 2D or planar surface system vaporizer is inefficient and performs poorly, since it is unable to heat or vaporize the interior regions of the load chamber; or 2) to overcome this, the 2D or planar surface system is run hotter, which has the alternate disadvantage that the vapor constrained at the 2D or planar surface gets overheated, leading to decomposition byproducts; poor taste as perceived by the user; and a loss of vaporizer delivery and energy efficiency. Insofar as these conditions are poor when considered in terms of what happens with a gas, these same effects are noticeably worse where the loaded materials contain liquids such as oils or resins, all of which have a higher viscosity and thus much worse motion and heating asymmetries.

In contrast with the above, the use of a fine mesh screen alleviates the above recited problems at once. Because a screen is gas permeable, there is no implied constraint in the degrees of freedom of motion of the vapor in the vicinity of the screen. This ensures a greater degree of symmetry of energy delivery to the loaded materials and thus more even vaporization without any attendant vapor overheating and decomposition effects and the user perceived vapor taste is preserved.

In addition, a three-dimensional (3D) screen in the shape of a trough, bowl, or the like as described in the embodiment herein provides the added benefit of having a heated surface area around the material by having a consistent heat energy for more evenly vaporizing the material without the need for high heat thereby enhancing the overall taste of the material and a more efficient method of vaporization.

Given the significant sensitivity of the user's ability to detect decomposition byproducts and other contaminants, the overall vapor taste improvement implied by the use of a gas permeable screen rather than any other type of impermeable or partially impermeable plate, vessel, or chamber, is a significant practical and functional improvement over all currently existing prior art.

In an exemplary mode of the device, to communicate electrical power evenly and at a high rate to the entire screen mesh, a plurality of conductive rods are engaged to a bottom surface of the screen mesh electrically. Electrical power from the battery is communicated through the entire length of the larger diameter rods at a high rate and thereafter evenly into the overhead supported fine conductive mesh. Of course wires or other methods or components to communicate power from the battery may also be employed. However, the large diameter rods relative to the mesh wire diameter have proved to yield desirable results.

A plastic cover over the vaporization chamber and underlying conductive mesh limits the oxygen to the material being vaporized to further insure that burning or flames do not occur during use. An exhaust tube in communication with the ignition chamber allows the user to selectively exhaust the vapors from the vaporization chamber during use.

With respect to the above description, before explaining at least one exemplary embodiment of the vaporizer device, it is to be understood that the description is not limited in its application to the details of operation nor the arrangement of the components set forth in the following description or illustrations in the drawings. The various disclosed components and arrangement thereof are capable of other embodiments and of being practiced and carried out in various ways, which will be apparent to those skilled in the art once they review this disclosure. Also, it is to be understood that the phraseology and terminology employed herein are for the purpose of description and should not be regarded as limiting.

Those skilled in the art will appreciate that the conception upon which this disclosure of a portable battery powered vaporizer is based may readily be utilized as a basis for designing of methods and systems for carrying out the several purposes of the presently disclosed vaporizer invention.

The objects and claims herein should be regarded as including such equivalent construction, steps, and methodology insofar as they do not depart from the spirit and scope of the present description. Further objectives of the invention will be brought out in the following part of the specification wherein detailed description is for the purpose of fully disclosing one exemplary embodiment of the invention without placing limitations thereon.

It is an object of the description, to provide an easily carried and employed battery-powered vaporizer that produces exhaustible vapors and reduces undesirable material and particulate therefrom. The benefits of using a fine mesh screen as the heating element, rather than a flat metal plate, are twofold: 1) there is much lower thermal mass, which leads to faster heat-up and cool-down time; and 2) there are no superheated vapor effects at the contact surface since the fine mesh screen permits contact gasses to readily escape.

These together with other objects and advantages that become subsequently apparent reside in the details of the construction and operation of the portable battery powered vaporizer device herein as more fully hereinafter described and claimed, reference being had to the accompanying drawings forming a part thereof, wherein like numerals refer to like parts throughout.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION

Figure 1:
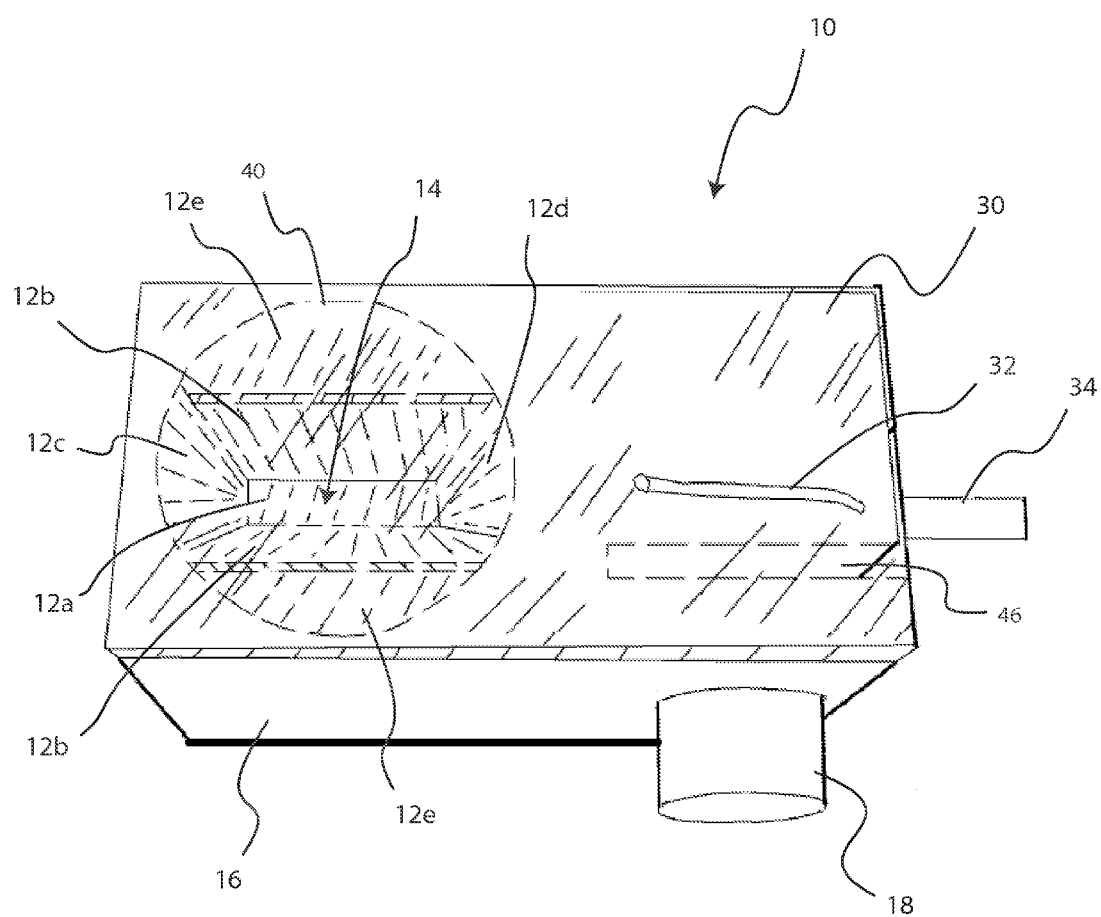
FIG. 1 is a perspective view of a device illustrating a transparent rotatable shield covering a vaporization chamber and a battery in electrical communication with a conductive element.

Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the invention to the precise form and configuration shown in the drawings and disclosed in the following detailed description.

Figure 2:
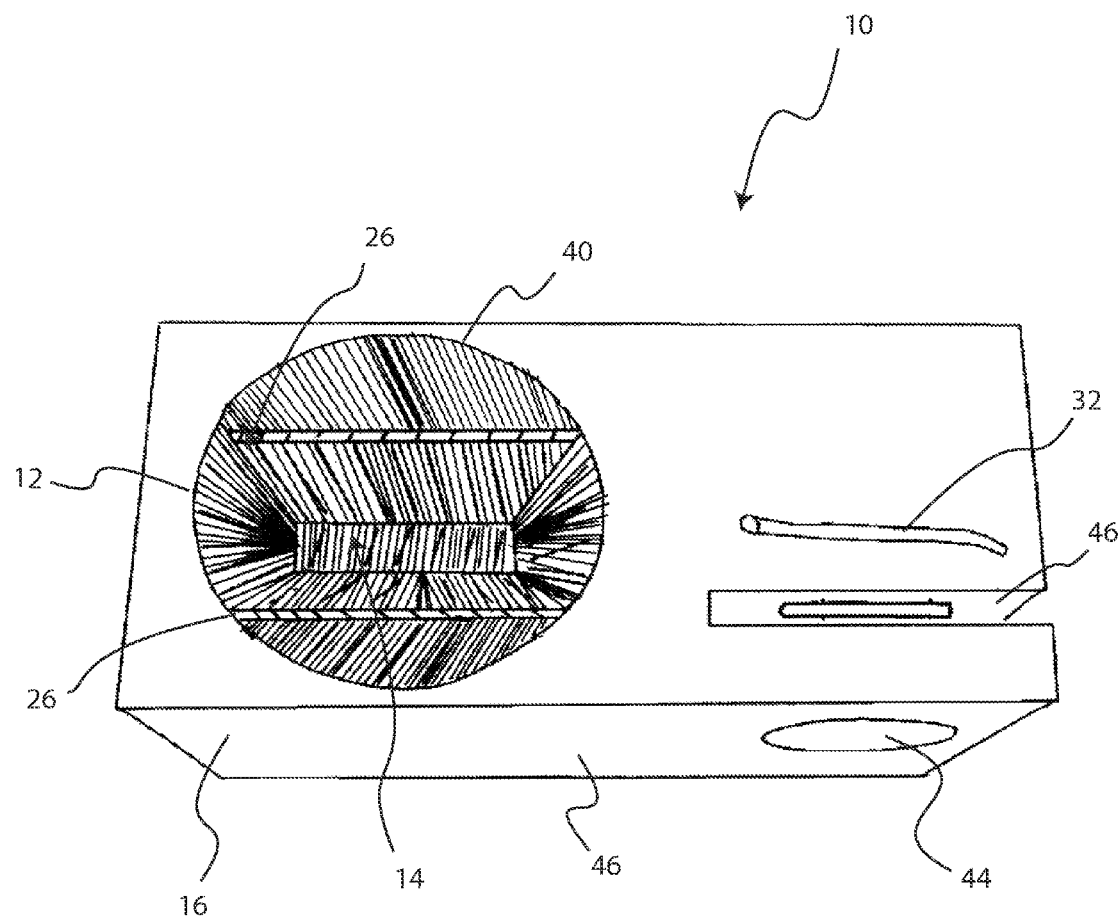
FIG. 2 is a perspective view of the device of FIG. 1 illustrating the transparent shield and battery removed from electrical communication with the conductive engagement.
Figure 3:
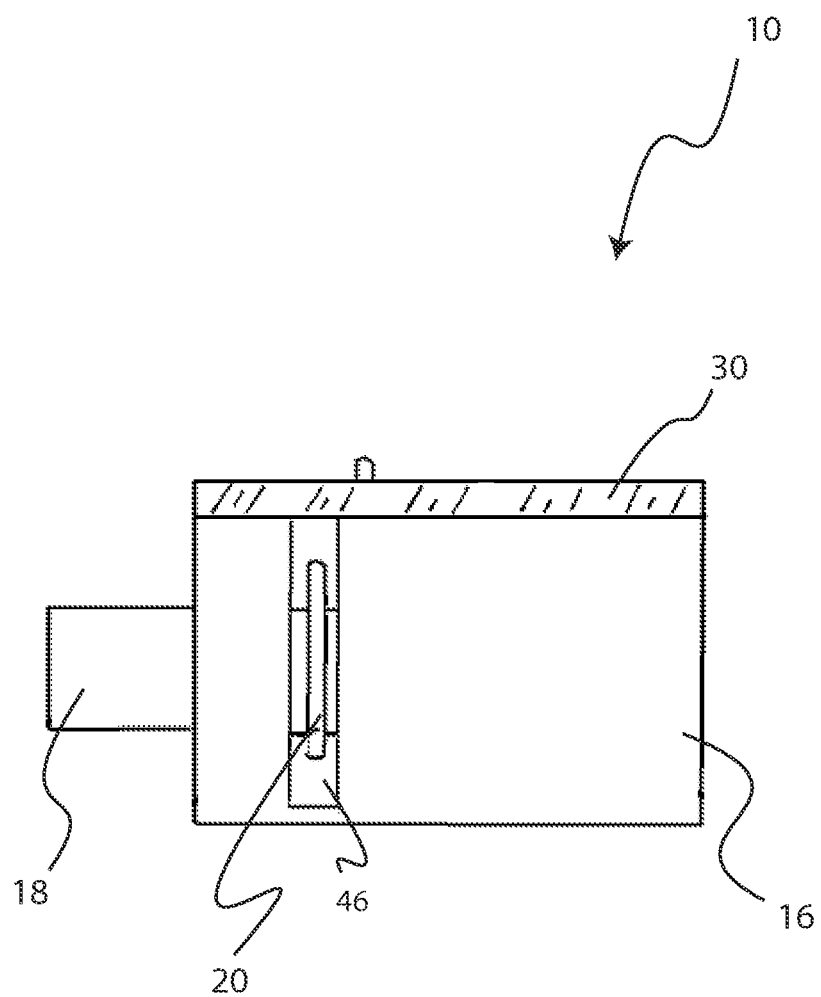
FIG. 3 is a front view of the device of FIG. 1.
Figure 4:
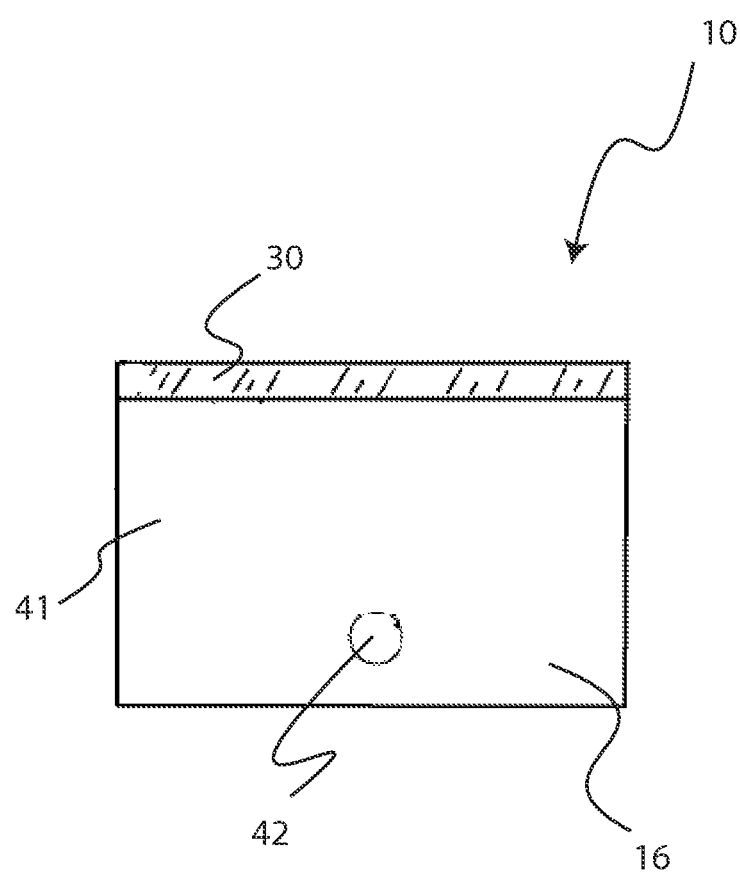
FIG. 4 is a back view of FIG. 1 illustrating a mouth-engageable tube employed to exhaust vapors from the vaporization chamber.

Referring now to FIGS. 1-5, a vaporizer 10 provides a highly portable vaporizer for herbs and other materials employed in combination herewith.

A controlled heat source without flame is provided by a fine mesh conductive screen 12, which is placed within the vaporization chamber 14 and adapted to be in direct contact with the overhead material (not shown) being vaporized. The benefits of using a fine mesh screen 12 as the heating element, rather than a flat metal plate, are twofold: 1) there is much lower thermal mass, which leads to faster heat-up and cool-down time; and 2) there are no superheated vapor effects at the contact surface since the fine mesh screen 12 permits contact gasses to readily escape.

The fine mesh screen 12 is provided in a size between 90 mesh and 900 mesh for properly heating the overhead material while providing a screen or filter function for the material. Burning as noted is prevented and the problems associated therewith. The mesh screen 12 is formed in a trough-like configuration having a bottom mesh surface 12a, longitudinal length mesh walls 12b in a generally 45 degree orientation to the bottom mesh surface 12a, a front mesh surface 12c in a generally 45 degree orientation to the bottom mesh surface 12a, a rear mesh surface 12d in a generally 45 degree orientation to the bottom mesh surface 12a, and a top mesh surface 12e.

The fine mesh conductive screen 12 is positioned within the vaporization chamber 14 formed in a housing 16 and provides a direct support the material being vaporized overhead. Gravity helps to draw the material in a tighter direct contact with the conductive screen 12.

The fine mesh conductive screen 12 is heated by communicating electrical energy thereto and heats as a resistive load. The electrical energy causes a fast and substantially even heating of the surface of the conductive screen 12 thereby vaporizing the material it supports to elicit vapors from the material without burning it.

Electrical energy communicated to the fine mesh conductive screen 12 is provided at a low voltage and high current level to avoid injury to the user. In the provided exemplary embodiment, the fine mesh screen 12 is fabricated by either woven or knitted conducting materials such as one or a combination of conductive materials including copper, nickel, iron, or any wire alloys composed of these elements or the like, such as steel and stainless steel or the like.

The electrical energy source is provided by batteries 18 adapted for a removable conductive engagement with the fine mesh screen 12 using a battery mount 20. Part of the mount 20 contacts the ground of the battery 18 and part of the mount contacts a positive surface of the battery 18. The electrical energy is conducted through the mount 20 to the fine mesh screen 12 to heat it in a resistive load thereon.

The vaporizer 10 communicates electrical power evenly and at a high rate to the entire screen meshes 12 by a plurality of conductive rods 26 that are in electrical communication with a surface of the screen mesh 12. Electrical power communicates through the entire length of the larger diameter rods 26 and enters the mesh screen 12 evenly and with high current. Other delivery methods to communicate electrical power from the battery 18 may also be employed however the large diameter rods 26 welded or otherwise electrically engaged to the screen mesh 12 yield desirable results and fast even heating.

A cover 30 formed of plastic or other material is rotatably engaged to the top of the housing 16 and rotates to both provide access to and cover the vaporization chamber 14. The cover 30 is secured to the surface of housing 16 by a mechanical spring mechanism 32. The cover 30 limits oxygen communication to the material being vaporized to further reduce chances of combustion.

An exhaust tube 34 disposed within an exhaust opening and selectively placed in communication with the vaporization chamber 14 is adapted to exhaust the vapors formed by the vaporization process in the vaporization chamber 14 during use.

In one exemplary embodiment, the vaporizer 10 is fabricated by selecting a raw stock of wood that is milled to a desired thickness, width and length to form a desired shape. In the embodiment illustrated in FIGS. 1-4, a rectangular block is selected out of the many possible shapes and sizes contemplated. An aperture 40 forming the vaporization chamber 14 is drilled into the top surface of the housing 16. The aperture 40 is wide enough to accept the fine mesh screen 12 and deep enough to allow air passage both above and below the fine mesh screen 12.

Two rod apertures are drilled for the two conducting rods 26 at a housing face 41 opposite the vaporization chamber 14 that are evenly spaced on either side of the longitudinal length center-line of the housing 16. These two rod apertures are later sealed once the conducting rods 26 are inserted. A third aperture 42 is drilled for the exhaust tube 34 to the aperture 40 and adapted to allow the user to secure the exhaust tube in the aperture 42 and communicate with the material on the conductive screen 12.

A battery aperture 44 is drilled from the longitudinal side 46 of the housing 16 across one of the rod apertures to approximately the location of the second rod aperture and is adapted to permit selective communication of the second conductive rod 26 with the positive terminal connector on the battery 18. The battery aperture 44 is of a diameter as needed to admit the desired battery. The aperture 44 is located on the centerline of the housing 16 as measured between the upper and lower surfaces of the housing. The side of the housing 16 from which this aperture 44 is drilled and the rod aperture that it crosses vs. the rod aperture that it meets distinguishes the polarity of the two rod apertures: The crossed rod aperture will secure the negative terminal rod and the reached rod aperture secures the positive terminal rod.

A slot 46 with approximately the same width as that of the conductive rods 26 is cut in line with the negative conductive rod aperture, approximately ¼" short of the aperture 40 and generally perpendicular to the axis of the battery aperture 44. The positive and negative conductive rods 26 are cut to length and inserted into their respective apertures. The fine mesh conductive screen 12 is cut to fit into aperture 40, formed into a trough shape, and placed in electrical communication with the conductive rods 26 by any technique including but not limited to thermal fusion techniques. The cover 30 is cut to generally cover the upper surface of the housing 16 and secured by the spring mechanism 32 thereto.

A method of fabricating the vaporizer 10 is also contemplated by performing any of the following steps in any order: 1) providing the housing 16 with the vaporizing chamber 14 formed therein; 2) placing the fine mesh conductive screen 12 inside the vaporizing chamber 14 for generation of heat through electrical resistance wherein at least a portion of the fine mesh conductive screen 12 is formed into a three-dimensional shape; 3) securing the conductive rods 26 to the fine mesh conductive screen 12 wherein one of the conductive rods 26 is adapted to be in electrical communication with the positive terminal of the battery 18; 4) installing a cover 30 in mechanical communication with a surface of the housing 16 for covering the aperture 40 to the vaporizing chamber 14; and 5) providing the exhaust aperture 42 in the housing 16 for evacuating vapors by a user. Additional steps may include any one or more of the following steps: 6) sizing the fine mesh conductive screen 12 between 90 mesh and 900 mesh; 7) forming the three-dimensional shape in a generally trough-like shape or a generally bowl-like shape; and 8) forming the fine mesh conductive screen 12 by weaving or knitting a conductive material.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A vaporizer comprising: (a) a housing having an outer surface; (b) a vaporization chamber formed in the outer surface of the housing; (c) a first electrically conductive rod that extends through a first rod aperture and into the vaporization chamber; (d) a second electrically conductive rod that extends through a second rod aperture and into the vaporization chamber; (e) a fine mesh conductive screen disposed inside said vaporization chamber and affixed to the first and second rods in electrical communication with the rods; (f) an exhaust aperture extending through the housing from the outer surface of the housing into the vaporization chamber; and (g) a battery aperture extending into the housing from the outer surface and intersecting the first and second rod apertures within the housing, the battery aperture being adapted to receive a battery, wherein, upon insertion of a battery into the battery aperture, the battery will contact the first and second electrically conductive rods and pass current to the mesh conductive screen to heat the screen through electrical resistance.

2. The vaporizer of claim 1, wherein a cover is in mechanical communication with a surface of said housing for covering the vaporization chamber.

3. The vaporizer of claim 1, wherein said fine mesh conductive screen is woven or knitted from a conductive material.

4. The vaporizer of claim 3, wherein said conductive material is selected from a group of at least one of a copper, a nickel, an iron, an alloy, a steel, and a stainless steel.

5. The vaporizer of claim 1, wherein said battery is selected from a group consisting of a standard AA battery or a standard AAA battery.

6. The vaporizer of claim 1, wherein at least a portion of said fine mesh conductive screen is formed in a generally trough-like shape.

7. The vaporizer of claim 1, wherein at least a portion of said fine mesh conductive screen is formed into a three-dimensional shape.

8. The vaporizer of claim 7, wherein said fine mesh conductive screen is sized between 90 mesh and 900 mesh.

9. A vaporizer comprising: a housing with an outer surface and a vaporization chamber formed in the outer surface thereof; a fine mesh conductive screen disposed inside said vaporization chamber; a first conductive rod and a second conductive rod in communication with said fine mesh conductive screen, with the mesh being attached to the first and second rods; a battery aperture in the housing adapted to receive a battery therein, the battery aperture intersecting the said first and second conductive rods, wherein, upon insertion of a battery into the battery aperture, the battery will contact the first and second electrically conductive rods and pass current to the mesh conductive screen to heat the screen through electrical resistance; a cover in mechanical communication with a surface of said housing for covering the vaporizing chamber; and an exhaust aperture in said housing extending between the surface of the housing and the vaporization chamber at a point below the fine mesh conductive screen.

10. The vaporizer of claim 9, wherein said fine mesh conductive screen is sized between 90 mesh and 900 mesh.

11. The vaporizer of claim 9, wherein the screen mesh has a generally trough-like shape.

12. The vaporizer of claim 9, wherein said fine mesh conductive screen is woven or knitted from a conductive material.

13. The vaporizer of claim 9, wherein the housing is a rectangular block having a top side, a bottom side, a first side, a second side, a first end, a second end and a longitudinal axis extending between the first end and the second end substantially parallel to the first and second sides, and wherein the battery aperture extends through the first side and across the longitudinal axis.

14. The vaporizer of claim 13, wherein the first and second rod apertures extend substantially parallel to the longitudinal axis on opposite sides of the longitudinal axis.

15. The vaporizer of claim 13, wherein the housing is made of wood.

\* \* \* \* \*